(12) United States Patent
Braeutigam

(10) Patent No.: US 7,846,421 B2
(45) Date of Patent: Dec. 7, 2010

(54) STYLING WAX COMPOSITION

(75) Inventor: Ina Braeutigam, Darmstadt (DE)

(73) Assignee: KPSS-Kao Professional Salon Services GmbH, Darmstadt (DE)

( * ) Notice: Subject to any disclaimer, the term of this patent is extended or adjusted under 35 U.S.C. 154(b) by 640 days.

(21) Appl. No.: 11/470,400

(22) Filed: Sep. 6, 2006

(65) Prior Publication Data
US 2007/0053847 A1 Mar. 8, 2007

(30) Foreign Application Priority Data
Sep. 8, 2005 (EP) ................... 05019534

(51) Int. Cl.
*A61K 8/00* (2006.01)
*A61K 8/30* (2006.01)
*A61K 9/12* (2006.01)

(52) U.S. Cl. .................... 424/47; 424/43; 424/70.31

(58) Field of Classification Search .................... 424/47, 424/70.31, 43; 514/734
See application file for complete search history.

(56) References Cited

U.S. PATENT DOCUMENTS

| 6,231,844 B1 | 5/2001 | Nambu |
| 6,589,517 B1 * | 7/2003 | McKelvey et al. ......... 424/70.1 |
| 6,635,240 B1 | 10/2003 | Bolich, Jr. et al. |
| 2002/0122811 A1 | 9/2002 | Stein et al. |
| 2004/0052744 A1 | 3/2004 | Maillefer et al. |

FOREIGN PATENT DOCUMENTS

| DE | 25 21 960 A1 | 4/1976 |
| DE | 28 11 010 A1 | 9/1978 |
| DE | 32 17 059 A1 | 11/1982 |
| EP | 0 337 354 A1 | 10/1989 |
| EP | 0 524 612 A2 | 1/1993 |
| EP | 0 640 643 A2 | 3/1995 |
| WO | 93 10748 | 6/1993 |
| WO | 94 16677 | 8/1994 |
| WO | 96 32093 | 10/1996 |

OTHER PUBLICATIONS

Goldwell, GMBH, DE 20018677, Hair-Care Compositions Acting as Matte Waxes, Derwent Abstracts, Mar. 7, 2002, pp. 1-3.*

* cited by examiner

*Primary Examiner*—Johann R Richter
*Assistant Examiner*—Andriae M Holt
(74) *Attorney, Agent, or Firm*—Norris McLaughlin & Marcus PA

(57) ABSTRACT

The present invention relates to styling wax composition applied as aerosol spray with improved styling benefits, especially with excellent shine and hold and also excellent elasticity. The inventors of the present invention have found out surprisingly that an aqueous or aqueous-alcoholic hair styling composition based on at least one film forming polymer selected from anionic, non-ionic, amphoteric and cationic ones comprising at least one polyalkyleneglycol ether of fatty acid glyceride or partial glyceride with at least 30 alkylene glycol units at a concentration of 3 to 25% by weight calculated to total composition, at least one ethoxylated fatty alcohol with saturated or unsaturated alkyl chains of 12 to 18 C atoms and with 1 to 3 ethoxy units as the wax component at a concentration 1 to 15% by weight calculated to total composition, is possible to spray onto hair from an aerosol can containing further a propellant selected from dimethylether, 1,2-difluoroethane and their mixture at a concentration of at least 30% by weigh calculated to total composition.

11 Claims, No Drawings

STYLING WAX COMPOSITION

The present invention relates to styling wax composition applied as an aerosol spray with improved styling benefits, especially with excellent shine and hold and also excellent elasticity.

Styling compositions have been known for decades. They are used after usual hair conditioning cycle to give hair better and long lasting hold, to improve hair volume or simply to fix the hair so that the hair does not move naturally.

Wax type of products has also been used widely. They are usually a thick paste and applied onto hair by hand. Such kind of hand application brings problems of hygiene and especially difficult in handling and spreading the rests of product all around cloths, baths simply by touching without being aware of. It is, therefore, highly desirable to develop new application forms for wax containing styling products.

The inventors of the present invention have found out surprisingly that an aqueous or aqueous-alcoholic hair styling composition based on at least one film forming polymer selected from the anionic, non-ionic, cationic and/or amphoteric or zwitterionic ones comprising at least one polyalkyleneglycol ether of fatty acid glyceride or partial glyceride with at least 30 alkylene glycol units at a concentration of 3 to 25% by weight calculated to total composition, at least one ethoxylated fatty alcohol with saturated or unsaturated alkyl chains of 12 to 18 C atoms and with 1 to 3 ethoxy units as the wax component at a concentration 1 to 15% by weight calculated to total composition, is possible to spray onto hair from an aerosol can containing further a propellant selected from dimethylether, 1,2-difluoroethane and their mixture at a concentration of at least 30% by weight calculated to total composition. In the above with the total composition it is meant the liquid composition with propellant.

To the inventor's surprise, the above composition is transparent at a transparent at a temperature range of 25° C. to 35° C. as judged by naked eye in a vessel with a solution thickness of 1 cm. At the temperatures below 25° C. the composition becomes turbid.

It has further been observed that at storage temperature range of 25° C. to 35° C. the composition is a single phase and as well as in an aerosol can including the propellant single phase composition is obtained even et temperatures as low as 5° C.

Thus, subject of the present invention is an aqueous or aqueous-alcoholic aerosol hair styling composition based on at least one film forming polymer selected from the anionic, non-ionic, cationic and/or amphoteric or zwitterionic ones comprising at least one polyalkyleneglycol ether of fatty acid glyceride or partial glyceride with at least 30 alkylene glycol units at a concentration of 3 to 25% by weight calculated to total composition, at least one ethoxylated fatty alcohol with saturated or unsaturated alkyl chains of 12 to 18 C atoms and with 1 to 3 ethoxy units as the wax component at a concentration 1 to 15% by weight calculated to total composition, and a propellant selected from dimethylether and 1,2-difluoroethane at a concentration of at least 30% by weigh calculated to total composition. In the above with the total composition it is meant the liquid composition with propellant.

Further object of the invention is that a single phase and transparent, at temperatures above 25° C. in a thickness of 1 cm judged by naked eye, aqueous or aqueous-alcoholic aerosol hair styling composition based on at least one film forming polymer selected from the anionic, non-ionic, cationic and/or amphoteric or zwitterionic ones comprising at least one polyalkyleneglycol ether of fatty acid glyceride or partial glyceride with at least 30 alkylene glycol units at a concentration of 3 to 25% by weight calculated to total composition, at least one ethoxylated fatty alcohol with saturated or unsaturated alkyl chains of 12 to 18 C atoms and with 1 to 3 ethoxy units as the wax component at a concentration 1 to 15% by weight calculated to total composition, and a propellant selected from dimethylether and 1,2-difluoroethane at a concentration of at least 30% by weight calculated to total composition. In the above with the total composition it is meant the liquid composition with propellant.

Compositions of the present invention is packed into an aerosol can and applied onto dry hair by spraying from an appropriate distance. It has been observed that application of the liquid composition without propellant using a mechanical pump is as a rule possible but gives difficulties in terms of size of the sprayed droplets and furthermore causes unwanted effects on hair, overwetting. Therefore, it is the preferred application, if not only, that aqueous or aqueous-alcoholic aerosol hair styling composition based on at least one film forming polymer selected from the anionic, non-ionic, cationic and/or amphoteric or zwitterionic ones comprising at least one polyalkyleneglycol ether of fatty acid glyceride or partial glyceride with at least 30 alkylene glycol units at a concentration of 3 to 25% by weight calculated to total composition, at least one ethoxylated fatty alcohol with saturated or unsaturated alkyl chains of 12 to 18 C atoms and with 1 to 3 ethoxy units as the wax component at a concentration 1 to 15% by weight calculated to total composition, is principally applied by spraying from an aerosol can and for pressurising dimethyl ether, 1,2-difluoroethane and their mixture are found to be appropriate at a concentration of at least 30% by weight, calculated to total concentration.

It has as well been observed that use of other propellants such as gaseous alkanes causes separation (instability) and makes uniform application impossible, therefore such kind of propellants must be excluded form the compositions of the present invention.

Concentration of propellant varies between 30 and 65%, preferably 35 to 60%, more preferably 40 to 55% and most preferably 40 to 50% by weight calculated to total composition including propellant.

Preferred polyalkyleneglycol ether of fatty acid glyceride or partial glyceride with at least 30 polyalkylene units are with 30 to 1000, preferably 30 to 500, more preferably 30 to 200 and most preferably 40 to 100 polyethyleneglycol units. Examples to those are PEG-30 hydrogenated castor oil, PEG-35 hydrogenated castor oil, PEG-40 hydrogenated castor oil, PEG-45 hydrogenated castor oil, PEG-50 hydrogenated castor oil, PEG-55 hydrogenated castor oil, PEG-60 hydrogenated castor oil, PEG-65 hydrogenated castor oil, PEG-80 hydrogenated castor oil, PEG-100 hydrogenated castor oil, PEG-200 hydrogenated castor oil, PEG-35 castor oil, PEG-50 castor oil, PEG-55 castor oil, PEG-60 castor oil, PEG-80 castor oil, PEG-100 castor oil, PEG-200 castor oil. Additional examples of similar compounds can be found in the cosmetic ingredient dictionaries and cosmetic textbooks. It is the preferred components that the polyethylengylcol ethers of fatty acid glycerides or partial glycerides is in the form of a liquid or semisolid and further preferably having a melting point below 35° C., more preferably below 30° C.

Concentration of polyalkyleneglycol ether of fatty acid glyceride or partial glyceride with at least 30 polyalkylene units is preferably in the range of 3 to 20%, more preferably 4 to 15% and most preferably 5 to 15% and even most preferably 8 to 14% by weigh calculated to total composition including propellant.

Suitable examples to fatty alcohol ethoxylates as the wax compound are Ceteareth-2, Ceteareth-3, Ceteth-1, Ceteth-2, Ceteth-3, Myreth-2, Myreth-3, Oleth-2 and Oleth-3.

Concentration of these wax components in the compositions of the present invention is preferably in the range of 2 to 12%, more preferably 3 to 10% and most preferably 3 to 8% by weight calculated to total composition including propellant.

The compositions of the present invention comprise at least one film forming polymer selected from the anionic, non-ionic, cationic and/or amphoteric or zwitterionic ones. The most preferred ones are the non-ionic polymers. In the selection of the suitable film forming polymers it is important that clarity of the solution (composition) after preparation of the solution and before confectioning into an aerosol can should be controlled at a temperature above 25° C. with a solution thickness of 1 cm. In the case that the solution is turbid this may indicate an incompatibility, which may raise further problem when confectioned as an aerosol product.

Non-ionic polymers are selected from the ones soluble in water and/or in alcohol water mixtures, at any ratio. Under the definition of soluble in alcohol and alcohol water mixture, it should be understood that the polymer is soluble in lower alcohols such as ethanol, n-propanol or isopropanol and in their mixtures with water, at any ratio Suitable non-ionic polymer is first of all vinylpyrrolidon polymers either homopolymers or copolymers with, especially, vinylacetate. Those are known with the trade name "Luviskol" as homopolymers Luviskol K 30, K 60 or K 90 as well copolymers Luviskol VA 55, VA 64 from BASF AG.

Natural non-ionic polymers are as well suitable for the composition of the present invention. Those are such as cellulose, chitosan, guar gum, neutralised shellac and their derivatives.

As amphoteric polymers which can be used alone or in mixture with at least one additional nonionic polymer, reference is here made in particular to copolymers of N-octyl acrylamide, (meth)acrylic acid and tert.-butyl aminoethyl methacrylate of the type "Amphomer®"; copolymers from methacryloyl ethyl betaine and alkyl methacrylates of the type "Yukaformer®", e.g. the butyl methacrylate copolymer "Yukaformer® Am75"; copolymers from monomers containing carboxyl groups and sulfonic groups, e.g. (meth)acrylic acid and itaconic acid, with monomers such as mono- or dialkyl aminoalkyl (meth)acrylates or mono- or dialkyl aminoalkyl(meth)acrylamides containing basic groups, in particular amino groups; copolymers from N-octyl acrylamide, methyl methacrylate, hydroxypropyl methacrylate, N-tert.-butyl aminoethyl-methacrylate and acrylic acid, as well as the copolymers known from U.S. Pat. No. 3,927,199.

Suitable anionic polymers alone or in combination with non-ionic polymers are vinyl alkyl ether, in particular methyl vinyl ether/maleic acid copolymers, obtained by hydrolysis of vinyl ether/maleic anhydride copolymers, distributed under the trade name "Gantrez® AN or ES". These polymers may also be partly esterified, as for example, "Gantrez® ES 225" or "ES 435", the ethyl ester of an ethyl vinyl ether/maleic acid copolymer, or the butyl or isobutyl ester thereof.

Further useful anionic polymers are in particular vinyl acetate/crotonic acid or vinyl acetate/vinyl neodecanoate/crotonic acid copolymers of the type "Resyn®"; sodium acrylate/vinyl alcohol copolymers of the type "Hydagen® F", sodium polystyrene sulfonate, e.g. "Flexan® 130"; ethyl acrylate/acrylic acid/N-tert.-butyl acrylamide copolymers of the type "Ultrahold®"; vinyl pyrrolidone/vinyl acetate/itaconic acid copolymers, acrylic acid/acrylamide copolymers or the sodium salts thereof of the type "Reten®"; etc.

Composition of the present invention can comprise cationic polymers alone or in combination with non-ionic polymer. Those are cationic cellulose type polymers know as Polymer JR type from Amerchol such as Polyquaternium 10 or cationic guar gum known with trade name Jaguar from Rhone-Poulenc and chemically for example Guar hydroxypropyl trimonium chloride. Furthermore. chitosan and chitin can also be included in the compositions as cationic natural polymers.

Furthermore, those cationic polymers known with their CTFA category name Polyquaternium may as well be added into the compositions of the present invention. Typical examples of those are Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46.

As well those polymers known with their CTFA category name Quaternium can as well be suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

In this context, reference is also made to the cationic polymers disclosed in DE 25 21 960, 28 11 010, 30 44 738 and 32 17 059, as well as to the products described in EP-A 337 354 on pages 3 to 7, It is also possible to use mixtures of various cationic polymers.

The cationic polymers also include the quaternized products of graft polymers from organopolysiloxanes and polyethyl oxazolines described in EP-A 524 612 and EP-A 640 643. Among these especially preferred is the compound know with the INCI name Polysilicone-9.

The most preferred film forming polymers are non-ionic polymers and form them VP/VA copolymer is particularly preferred.

Concentration of polymers of anionic, cationic, non-ionic and/or amphoteric or zwitterionic character is in the range of 1-20%, preferably 2-15% and more preferably 3-12% and most preferably 4-10% by weight, calculated to the total composition including propellant.

The composition of the present invention can comprise polyols at a concentration of 0.5 to 15%, preferably 1 to 10%, more preferably 5 to 10% by weight calculated to the total concentration including propellant. The most preferred ones are glycerine, propylene glycols, butylene glycol and hexylene glycol. Further suitable one is sorbitol. It is also the preferred embodiment of the present invention that the compositions comprise at least two different polyols such as glycerine together with propylene or hexylene or butylene glycols.

The compositions of the present invention can contain one or more organic solvents within the scope of the invention, Suitable ones are ethanol, propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. The most preferred organic solvents are ethanol, isopropanol and propanol without limiting the scope. Concentration of solvents is up to 40%, more preferably 10 to 35% and most preferably 20 to 30% by weight calculated to total composition including propellant.

In a preferred embodiment of the present invention, compositions comprise at least one organic solvent, preferably ethanol or ethanol in mixture with isopropanol.

The compositions according to the present invention may comprise at least one silicone oil. Preferred silicone oils are known with their INCI name as dimethicone, dimethiconol, cyclomethicone and phenyltrimethicone. Commercially, they are available from various companies for example Dow Corning with the known DC series, Wacker Chemie and Toray silicones. All commercially available non volatile silicones are suitable in the compositions of the present invention. Examples to those are DC 200 series, DC1401, DC 1403, DC 1501 and DC 1503. Concentration of silicone oils in the compositions of the present invention is typically between 0.1 to 5%, preferably 0.2 to 4% more preferably 0.5. to 3% and most preferably 0.5 to 2% by weight calculated to total composition including propellant.

Cationic silicones know with INCI name as amodimethicone can as well be contained in the compositions of the present invention. Commercially it is available under the trade name DC 949 in emulsified form in mixture with a nonionic surfactant and a cationic surfactant.

Cationic surfactants may as well be incorporated into the styling compositions of the present invention. The cationic surfactants useful in the compositions are according to the general formula below:

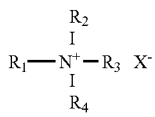

where $R_1$ is a saturated or unsaturated, branched or non-branched alkyl chain with 8-22 C atoms or

where $R_5$ is saturated or unsaturated, branched or non-branched alkyl chain with 7-21 C atoms and n has typical value of 0-4 or

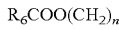

where $R_6$ is saturated or unsaturated, branched or non-branched alkyl chain with 7-21 C atoms and n has typical value of 0-4, and $R_2$ is a hydrogen, lower alkyl chain with 1 to 4 carbon atoms, saturated or unsaturated, branched or non-branched alkyl chain with 8-22 C atoms or

where $R_5$ is saturated or unsaturated, branched or non-branched alkyl chain with 7-21 C atoms and n has typical value of 0-4 or

where $R_6$ is saturated or unsaturated, branched or non-branched alkyl chain with 7-21 C atoms and n has typical value of 0-4, and $R_3$ and $R_4$ are independent from each other H or lower alkyl chain with 1 to 4 carbon atoms, and X is chloride, bromide or methosulfate.

It should be noted that quaternary ammonium compounds with single alkyl chain are preferred. Suitable cationic surfactants and or conditioning agents are, for example, long-chain quaternary ammonium compounds which can be used alone or in admixture with each other, such as cetyl trimethyl ammonium chloride, myristoyl trimethyl ammonium chloride, trimethyl cetyl ammonium bromide, stearyl trimethyl ammonium chloride, dimethyl stearyl ammonium chloride, dimethyl dihydrogenated tallow ammonium chloride, stear trimonium chloride, dipalmitoyl dimonium chloride, distearyl dimethyl ammonium chloride, stearamidopropyl trimonuim chloride and dioleoylethyl dimethyl ammonium methosulfate, etc.

From the above quaternary ammonium compounds disclosed with the general formula, suitable ones are those compounds known per se and are on the market, for example, under the trade names "Schercoquat®", "Dehyquart® F30" and "Tetranyl®". Use of these compounds, the so-called "esterquats", in hair care compositions is described, for example, in WO-A 93/107 48, WO-A 92/068 99 and WO-A 94/166 77, wherein, however, there is no reference made to the combinations according to the present invention and the advantageous properties thereof.

Again from the above quaternary ammonium compounds disclosed with the above general formula, suitable ones are these compounds are known per se and on the market, for example, under the trade name "INCROQUAT® HO" or "OCS". Those compounds are known with a general ingredient category under "amidoquat" in the cosmetic industry.

Concentration of at least one cationic surfactant of the above general formula is in the range of 0.01 to 2%, preferably 0.05 to 1.5% by weight and more preferably 0.1 to 1% by weight calculated to total composition.

Composition of the present invention comprises one or more natural and/or synthetic oil and/or mineral oil at a concentration of 0.01% to 2%, preferably 0.05 to 1.5% and more preferably 0.1 to 1.0%, most preferably 0.2 to 1.0% by weight calculated to total composition including propellant, Suitable natural oils are such as avocado oil, coconut oil, palm oil, sesame oil, peanut oil, whale oil, sunflower oil, almond oil, peach kernel oil, wheat germ oil, macadamia nut oil, night primrose oil, jojoba oil, castor oil, or also olive oil, soya oil, and the derivatives thereof. Mineral oils such as paraffin oil and petrolatum are suitably contained within the scope of the present invention, It should as well be noted that hair treatment compositions can contain mixture of one or more natural oils and mineral oil.

Further, suitable synthetic oil components are in particular fatty alcohol fatty acid esters such as isopropyl myristate, palmitate, stearate and isostearate, oleyl oleate, isocetyl stearate, hexyl laurate, dibutyl adipate, dioctyl adipate, myristyl myristate, oleyl erucate, polyethylene glycol and polyglyceryl fatty acid esters, cetyl palmitate, etc.

The compositions according to the invention may also comprise further agents, such as proteins, for example bamboo protein, and protein hydrolyzates and polypeptides, e.g. keratin hydrolyzates, collagen hydrolyzates of the type "Nutrilan®" or elastin hydrolyzates, as well as, in particular vegetable, optionally cationized protein hydrolyzates, for example "Gluadin®".

Additional natural plant extracts can as well form part of the compositions of the present invention. Those are incorporated usually in an amount of about 0.01% to about 5%, preferably 0.05% to 3.5%, in particular 0.1% to 2% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, coconut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapon®" products, "Herbasol®", "Sedaplant®" and "Hexaplant®". Extracts and the preparation thereof are also described in "Hagers Handbuch der pharmazeutischen Praxis", $4^{th}$ Ed.

Compositions of the present invention may contain UV filters either for stabilization of the product colour and/or for protection of hair from environmental influences such as loss of elasticity, loss of hair colour (bleaching effect of sun light). Suitable UV-absorbing substance are 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2,2',4,4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2,2'-dihydroxy-4,4'-dimethoxy-5,5'-disulfobenzo-phenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof and/or 3-(4'-methyl benzylidene)-DL-campher.

The suitable amount of the UV-absorber ranges from about 0.01% to 1% by weight, calculated to the total composition. Attention should be paid to the stability and appearance especially when using UV filter as salts, e.g. anionic UV filter salts.

Viscosity of the compositions is as a rule very low and should not exceed in any case 100 mPa·s, preferably 30 to 70 mPa·s and more preferably 35 to 50 mPa·s measured at 25° C. with a Brookfield viscosimeter with Spindle 1 at a rotation speed of 40 rpm.

pH of the compositions measured before confectioning as aerosol product vary between 3 to 9, preferably 4 to 8 and more preferably 5 to 8 measured 25° C.

Compositions of the present invention may further comprise any compound needed for the application purposes and at the same time allowed for using in cosmetic products such as ceramides, sphingolipids, moisturizing agents, preservatives, chelating agents, radical scavengers, antioxidants, fragrance, dyestuffs and pH regulators.

Further object of the invention is process for styling hair with a composition of the present invention based on at least one film forming polymer selected from the anionic, nonionic, cationic and/or amphoteric or zwitterionic ones comprising at least one polyalkyleneglycol ether of fatty acid glyceride or partial glyceride with at least 30 alkylene glycol units at a concentration of 3 to 25% by weight calculated to total composition, at least one ethoxylated fatty alcohol with saturated or unsaturated alkyl chains of 12 to 18 C atoms and with 1 to 3 ethoxy units as the wax component at a concentration 1 to 15% by weight calculated to total composition, and a propellant selected from dimethylether and 1,2-difluoroethane at a concentration of at least 30% by weigh calculated to total composition including propellant, by applying the composition onto dry hair The following examples are to illustrate the invention and non-limiting.

EXAMPLE 1

|  | % by weight |
| --- | --- |
| VP/VA Copolymer | 6 |
| PEG-40 Hydrogenated castor oil | 5 |
| Ceteareth-3 | 2 |
| Ethanol | 20 |
| Water | 17 |
| Dimethyl ether | 50 |

Hair treated with the above composition, applied onto dry hair, is easy and quick to style, has intensive shine, and excellent hold and also shows excellent elasticity.

EXAMPLE 2

|  | % by weight |
| --- | --- |
| VP/VA Copolymer | 8 |
| PEG-40 Hydrogenated castor oil | 6 |
| Ceteth-3 | 3 |
| Ethanol | 20 |
| Water | 13 |
| Dimethyl ether | 35 |
| 1,2-difluoro ethane | 15 |

Similar results were observed as in the case of example 1.

EXAMPLE 3

|  | % by weight |
| --- | --- |
| VP/VA Copolymer | 8 |
| PEG-40 Hydrogenated castor oil | 6 |
| Steareth-3 | 3.2 |
| Ethanol | 22 |
| Water | 11 |
| Polysilicone-9 | 0.6 |
| Bambus extract | 0.1 |
| Dimethyl ether | 35 |
| 1,2-difluoro ethane | 15 |
| Fragrance | 0.1 |

Similar results were observed as in the case of example 1.

EXAMPLE 4

|  | % by weight |
| --- | --- |
| VP/VA Copolymer | 8 |
| PEG-60 Hydrogenated castor oil | 7 |
| Ceteareth-3 | 4 |
| Ethanol | 10 |

-continued

|  | % by weight |
|---|---|
| Isopropyl alcohol | 10 |
| Water | 11 |
| Polysilicone-9 | 0.6 |
| Bambus extract | 0.1 |
| Dimethyl ether | 35 |
| 1,2-difluoro ethane | 15 |
| Fragrance | 0.1 |
| Octylmethoxycinnamate | 0.2 |

The invention claimed is:

1. Aerosol hair styling composition containing at least one film forming polymer selected from non-ionic, anionic, amphoteric and cationic ones characterised in that it comprises
   - a—at least one polyalkyleneglycol ether of fatty acid glyceride or partial glyceride with at least 30 alkylene glycol units at a concentration of 3 to 25% by weight,
   - b—at least one ethoxylated fatty alcohol with saturated or unsaturated alkyl chains of 12 to 18 C atoms and with 1 to 3 ethoxy units as the wax component at a concentration 1 to 15% by weight, and
   - c—at least one propellant selected from the group consisting of dimethylether, 1,2-difluoroethane and mixtures thereof at a concentration of at least 30% by weight, all percentages calculated to total composition, wherein the composition is a single phase and is transparent at a temperature range of between 25° C. to 35° C., as seen in a vessel with a solution thickness of 1 cm.

2. Composition according to claim 1 characterised in that it comprises as component (a) polyethylenegylcolether of fatty acid glyceride or partial glyceride with 30 to 1000 polyethyleneglycol units.

3. Composition according to claim 1 that the component (a) is selected from PEG-30 hydrogenated castor oil, PEG-35 hydrogenated castor oil, PEG-40 hydrogenated castor oil, PEG-45 hydrogenated castor oil, PEG-50 hydrogenated castor oil, PEG-55 hydrogenated castor oil, PEG-60 hydrogenated castor oil, PEG-65 hydrogenated castor oil, PEG-80 hydrogenated castor oil, PEG-100 hydrogenated castor oil, PEG-200 hydrogenated castor oil, PEG-35 castor oil, PEG-50 castor oil, PEG-55 castor oil, PEG-60 castor oil, PEG-80 castor oil, PEG-100 castor oil and PEG-200 castor oil.

4. Composition according to claim 1 characterised in that component b is selected from Ceteareth-2, Ceteareth-3, Ceteth-1, Ceteth-2, Ceteth-3, Myreth-2, Myreth-3, Oleth-2 and Oleth-3.

5. Composition according claim 1 characterised in that it comprises as a film-forming polymer a non-ionic polymer VP/VA copolymer.

6. Composition according to claim 1 characterised in that it comprises at least one organic solvent at a concentration of up to 40% by weight, calculated to total composition.

7. Composition according to claim 1 characterised in that it comprises at least one cationic surfactant.

8. Composition according to claim 1 characterised in that it comprises at least one silicone compound.

9. Composition according to claim 1 characterised in that it comprises at least one UV filter.

10. Process for styling hair characterised in that a composition according to claim 1 is applied onto dry hair by spraying.

11. Composition according to claim 1 wherein component (a) is PEG-40 Hydrogenated castor oil, component (b) is Ceteth-3, and component (c) is a mixture of dimethylether and 1,2-difluoroethane.

* * * * *